United States Patent [19]

Kampe et al.

[11] 4,120,963
[45] Oct. 17, 1978

[54] CERTAIN PYRIDO[3,4-B]INDOLE-1-ONES

[75] Inventors: Wolfgang Kampe, Heddesheim; Martin Senn, Eppelheim; Max Thiel, Mannheim; Wolfgang Bartsch, Viernheim; Karl Dietmann, Mannheim-Vogelstang, all of Germany

[73] Assignee: Boehringer Mannheim GmbH, Mannheim, Germany

[21] Appl. No.: 798,736

[22] Filed: May 19, 1977

[30] Foreign Application Priority Data

Jun. 16, 1976 [DE] Fed. Rep. of Germany ....... 2626889

[51] Int. Cl.² .................. C07D 471/14; A61K 31/44
[52] U.S. Cl. .............................. 424/256; 260/294.8 B; 260/296 A
[58] Field of Search ..................... 260/294.8 B, 296 A; 424/256

[56] References Cited

U.S. PATENT DOCUMENTS

| 3,294,809 | 12/1966 | Shavel | 260/296 A |
| 3,301,867 | 1/1967 | Szmuszkovicz | 260/296 A |
| 3,304,309 | 2/1967 | Shavel et al. | 260/296 A |
| 3,466,293 | 9/1969 | Johnson et al. | 260/294.9 |

*Primary Examiner*—Alan L. Rotman
*Attorney, Agent, or Firm*—Burgess, Dinklage & Sprung

[57] ABSTRACT

New aminopropanol compounds of the formula

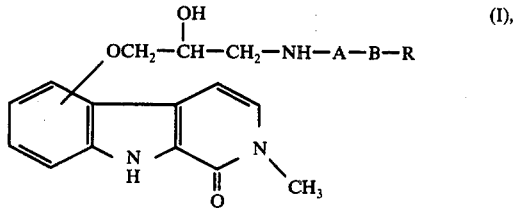

wherein
A is alkylene;
B is sulfur or a valency bond;
R is a straight-chained or branched lower alkyl; and the pharmacologically compatible salts thereof; are outstandingly effective adrenergic β-receptor inhibitors and useful in the treatment or prophylaxis of circulatory diseases.

8 Claims, No Drawings

CERTAIN PYRIDO[3,4-B]INDOLE-1-ONES

The present invention is concerned with new aminopropanol compounds and with therapeutic compositions and methods useful in the treatment of cardiac and circulatory diseases.

The new aminopropanol compounds according to the present invention are compounds of the general formula:-

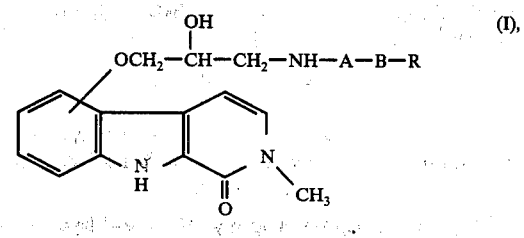

wherein
A is alkylene;
B is sulfur or a valency bond;
R is straight-chained or branched lower alkyl; and the pharmacologically compatible salts thereof.

The new compounds (I) according to the present invention, as well as their pharmacologically compatible salts, bring about an inhibition of adrenergic β-receptors and are, therefore, suitable for the treatment or prophylaxis of cardiac and circulatory diseases.

The alkylene radicals A are preferably branched and can contain 2 to 6 and preferably 2 to 4 carbon atoms. The alkyl radicals R can contain up to 4 carbon atoms.

The new compounds (I) according to the present invention can be prepared, for example, by one of the following methods:

(a) reaction of a compound of the general formula:

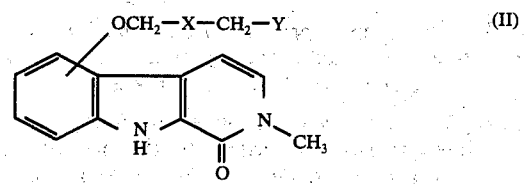

wherein Y is a reactive residue and X is a =C=O or -CH-Z group, Z being a hydroxyl group or, together with Y, representing an oxygen atom, with a compound of the general formula:

wherein A, B and R have the same meanings as above; or (b) reaction of a compound of the general formula:

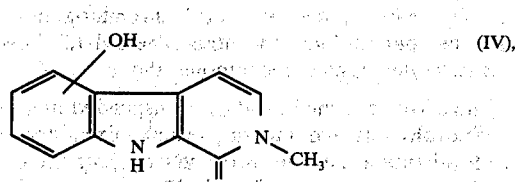

with a compound of the general formula:

wherein X, Y, A, B and R have the same meanings as above; or (c) when B represents a sulphur atom, reaction of a compound of the general formula:

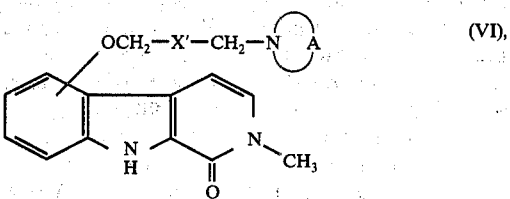

wherein A has the same meaning as above and X' is a =C=O or =CH—OH group, with a mercaptan of the general formula:

wherein R' is a hydrogen atom or has the same meaning as R, and, when R' represents a hydrogen atom, the product obtained is subsequently alkylated on the sulphur atom, and, when X or X' represents a =C=O group, the product obtained is subsequently reduced.

Compounds of general formula (I) obtained according to any of the above-described processes can, if desired, be subsequently converted into their pharmacologically compatible salts.

Reactive residues Y in the compounds of general formulae (II) and (V) are preferably acid residues, for example residues of hydrohalic or sulphonic acids.

The processes according to the present invention are preferably carried out in an organic solvent which is inert under the reaction conditions, for example, toluene, dioxan, ethylene glycol dimethyl ether, ethanol, n-butanol or dimethyl formamide, optionally in the presence of an acid-binding agent. However, the reaction can also be carried out by mixing the reaction components and either leaving the mixture to stand at ambient temperature or by heating it.

The reaction of compounds of general formula (IV) with compounds of general formula (V) according to process (b) is preferably carried out with the exclusion of oxygen in the presence of an acid acceptor. However, alkali metal salts of the hydroxy compounds of general formula (IV) can also be used.

The S-alkylation to be carried out when R' in the compounds of general formula (VII) is a hydrogen atom is preferably also carried out in a solvent of the abovementioned kind, with the exclusion of oxygen, using conventional S-alkylation agents.

When it is necessary to carry out the reduction of a =C=O group, this is preferably accomplished with the use of a complex metal hydride, for example sodium borohydride, or by means of catalytic hydrogenation, using a noble metal catalyst.

In order to convert the compounds of general formula (I) into their pharmacologically compatible salts, the compounds (I) are reacted, preferably in an organic solvent, with an equivalent amount of an inorganic or organic acid, for example, hydrochloric acid, hydrobromic acid, phosphoric acid, sulphuric acid, acetic acid, citric acid, maleic acid or benzoic acid.

For the preparation of pharmaceutical compositions, the compounds (I) are mixed in conventional manner with appropriate pharmaceutical carrier substances, aroma, flavoring and coloring materials and formed, for example, into tablets or dragees or, with the addition of appropriate adjuvants, suspended or dissolved in water or in an oil, for example olive oil.

The compounds (I) according to the present invention and their salts can be administered enterally or parenterally in admixture with liquid or solid pharmaceutical diluents or carriers. As injection medium, it is preferred to use water which contains the usual additives for injection solutions, such as stabilizing agents, solubilising agents or buffers. Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acid, high molecular weight fatty acids (such as stearic acid), gelatine, agar-agar and solid high molecular weight polymers (such as polyethylene glycols). Compositions suitable for oral administration can, if desired, contain flavoring and/or sweetening materials.

Preferred compounds according to the present invention include, in addition to those mentioned in the specific Examples, the following compounds:
5-(2-hydroxy-3-sec.-butylaminopropoxy)-1-oxo-2-methyl-1,2-dihydro-β-carboline; and
5-[2-hydroxy-3-(1-methylthioisopropylamino)-propoxy]-1-oxo-2-methyl-1,2-dihydro-β-carboline.

The following Examples are given for the purpose of illustrating the present invention:

EXAMPLE 1

5-(2-Hydroxy-3-isopropylaminopropoxy)-1-oxo-2-methyl-1,2-dihydro-β-carboline.

A solution of 6.8 g. 5-(2,3-epoxypropoxy)-1-oxo-2-methyl-1,2-dihydro-β-carboline in 50 ml. isopropylamine is left to stand for 2 days at ambient temperature. Subsequently, the solution is evaporated and the solid residue is dissolved in dilute acetic acid. The acetic acid solution is shaken out several times with a 1:1 mixture of ethyl acetate and diethyl ether. The aqueous phase is rendered alkaline with a 2N aqueous solution of sodium hydroxide, a precipitate thereby being obtained. This is filtered off with suction and recrystallized from ethyl acetate, with the addition of methanol. There are obtained 2.5 g. (about 30% of theory) 5-(2-hydroxy-3-isopropylaminopropoxy)-1-oxo-2-methyl-1,2-dihydro-β-carboline; m.p. 175° C.

For conversion into the acetate, the above-obtained base is dissolved in hot ethyl acetate and the stoichiometric amount of glacial acetic acid is added thereto. After cooling and evaporation of the greater part of the ethyl acetate, there is obtained a practically quantitative yield of 5-(2-hydroxy-3-isopropylaminopropoxy)-1-oxo-2-methyl-1,2-dihydro-β-carboline acetate; m.p. 182°-184° C.

EXAMPLE 2

5-(2-Hydroxy-3-tert.-butylaminopropoxy)-1-oxo-2-methyl-1,2-dihydro-β-carboline.

5.8 g. 5-(2,3-Epoxypropoxy)-1-oxo-2-methyl-1,2-dihydro-β-carboline are dissolved in a mixture of 100 ml. tert.-butylamine and 25 ml. ethylene glycol dimethyl ether. The solution is left to stand for 4 days at ambient temperature and then evaporated. The residue is taken up in dilute acetic acid and the acetic acid solution is shaken out with ethyl acetate.

The aqueous phase is rendered alkaline and shaken out with chloroform. After drying and treating with active charcoal, the chloroform solution is filtered and evaporated to give 3.3 g. (44% of theory) 5-(2-hydroxy-3-tert.-butylaminopropoxy)-1-oxo-2-methyl-1,2-dihydro-β-carboline; m.p. 217°-220° C.

The above-obtained base is dissolved in about 50 ml. methanol and mixed with 0.8 ml. glacial acetic acid. After the addition of about 50 ml. diethyl ether, a precipitate is slowly formed. This is filtered off with suction and dried to give 2.6 g. 5(2-hydroxy-3-tert.-butylaminopropoxy)-1-oxo-2-methyl-1,2-dihydro-β-carboline acetate; m.p. 221°-223° C. cl

EXAMPLE 3

5-[2-Hydroxy-3-(1-methylthio-2-methylisopropylamino)-propoxy]-1-oxo-2-methyl-1,2-dihydro-β-carboline.

3.8 g. 5-(2,3-Epoxypropoxy)-1-oxo-2-dihydro-β-carboline and 10.0 g. 1-methylthio-2-methylpropyl-2-amine are heated together on an oil bath until a homogeneous mixture is obtained. This is left to stand for 5 days at ambient temperature, then mixed with toluene and evaporated in a vacuum, finally for quite a long time at an elevated temperature. The residue is taken up in dilute acetic acid and filtered to remove undissolved material. The acetic acid solution is rendered alkaline and the precipitate thus obtained is filtered off with suction and recrystallized from isopropanol. The product obtained, which is still not quite pure, is dissolved in hot ethyl acetate and mixed with 0.4 ml. glacial acetic acid. The precipitate obtained is again recrystallized from ethyl acetate, with the addition of some glacial acetic acid and diethyl ether. There is finally obtained 1.5 g. (about 24% of theory) 5-[2-hydroxy-3-(1-methylthio-2-methylisopropylamino)-propoxy]-1-oxo-2-methyl-1,2-dihydro-β-carboline acetate; m.p. 138°-140° C.

The 5-(2,3-epoxypropoxy)-1-oxo-2-methyl-1,2-dihydro-β-carboline used as starting material in Examples 1 to 3 is obtained in the following manner:

21.6 g. 5-Methoxy-1-oxo-2-methyl-1,2-dihydro-β-carboline (prepared according to the method of G. Blaikie and W. H. Perkin jun., J. Chem. Soc., 125, 296/1924) are heated in a mixture of 150 ml. each of 47% aqueous hydrobromic acid and 40% hydrogen bromide in glacial acetic acid for 10 hours. The initially insoluble material thereby goes into solution. The reaction mixture is then poured into 1 liter water and the precipitate obtained is filtered off with suction. The residue is dissolved in 1 liter chloroform-methanol (1:1) and the solution is treated with active charcoal and subsequently evaporated. The solid residue is triturated with ethyl acetate/diethyl ether (1:1) and filtered off with suction. There are obtained 14.2 g. (about 70% of theory) chromatographically almost pure 5-hydroxy-1-oxo-2-methyl-1,2-dihydro-β-carboline, which decomposes above 300° C.

The above-obtained product is suspended in 100 ml. epichlorohydrin and the suspension mixed dropwise, while stirring at ambient temperature, over the course of about 6 hours, with 70 ml. 2N sodium methylate solution. The reaction mixture is further stirred for 2 days and then evaporated in a vacuum. The residue is taken up in 400 ml. chloroform/methanol (1:1) and the solution is treated with active charcoal, as well as with fullers' earth, and evaporated. The residue is successively recrystallized from ethyl acetate and ethanol. There are obtained 5.8 g. (about 33% of theory) 5-(2,3-epoxypropoxy)-1-oxo-2-methyl-1,2-dihydro-β-carboline, which slowly decomposes beyond about 250° C.

The following tests were carried out to determine the cardiac β-receptor blocking activity of certain test compounds by determining the inhibition of the heart beat frequency increase induced by intravenous administration of isoprenalin (=3,4-dihydroxy-α-[(isopropylamino)-methyl]-benzylalcohol).

The test compounds representative of the invention were the following:

| | | |
|---|---|---|
| Compound | I | 5-(2-hydroxy-3-isopropylaminopropoxy)-1-oxo-2-methyl-1,2-dihydro-β-carboline |
| Compound | II | 5-(2-hydroxy-3-tert.-butylaminopropoxy)-1-oxo-2-methyl-1,2-dihydro-β-carboline |
| Compound | III | 5-[2-hydroxy-3-(1-methylthio-2-methyl-isopropylamio)-propoxy]-1-oxo-2-methyl-1,2-dihydro-β-carboline |

As comparison compounds there were included:

| | |
|---|---|
| Compound A | 1-isopropylamino-3-(1-naphthoxy)-2-propanol (Propranolol) |
| Compound B | 1-(4-indolyloxy)-3-isopropylamino-2-propanol (Prindolol) |

These compounds were tested in the following manner:

The β-receptor blocking activity of the test compounds was tested on wake rabbits weighing between 2 to 3.5 kg and kept in wooden cages. EKG-electrodes were inserted into the hind quarters of the rabbits s.c. (II. lead) and the heart beat frequency was measured using an integrator (15 seconds) as a digital value. The test compounds were then infused through a small tube to the ear vein of the rabbits over a period of 15 minutes. 30 minutes after the fusion isoprenalin was injected intravenously at 1 μg/kg.

The results, set forth in terms of inhibition of isoprenalin tachycardia, are shown in the Table below:

TABLE

Blocking of Isoprenalin Tachycardia (1 μg/kg i.v.) in Wake Rabbits

| Test Substance | Dosage mg/kg i.v. | Heartbeat Frequency (min.) $x \pm s_x^-$ | ~DE 250* mg/kg i.v. |
|---|---|---|---|
| Control | without Iso-prenalin | 205 ± 9 | — |
| Control | with Iso-prenalin | 338 ± 10 | — |
| Compound A (Propranolol) | 0.01 | 342 ± 5 | |
| | 0.1 | 309 ± 9 | |
| | 0.25 | 259 ± 7 | 0.400 |
| | 0.5 | 248 ± 6 | |
| | 1.0 | 210 ± 8 | |
| | 4.0 | 191 ± 6 | |
| Compound B (Prindolol) | 0.005 | 318 ± 12 | |
| | 0.05 | 284 ± 7 | |
| | 0.1 | 361 ± 7 | 0.150 |
| | 0.5 | 220 ± 5 | |
| | 1.0 | 224 ± 5 | |
| Compound I | 0.001 | 331 ± 6 | |
| | 0.005 | 281 ± 7 | 0.010 |
| | 0.010 | 247 ± 5 | |
| | 0.100 | 216 ± 11 | |
| Compound II (Example 2) | 0.001 | 289 ± 10 | |
| | 0.005 | 255 ± 4 | 0.006 |
| | 0.010 | 237 ± 5 | |
| | 0.100 | 207 ± 7 | |
| Compound III (Example 3) | 0.003 | 335 ± 5 | |
| | 0.010 | 250 ± 11 | 0.010 |
| | 0.050 | 211 ± 10 | |

*Interpolated dosage which limits the frequency increase to 250 beats/min.

The above data show that the inventive compounds require much small dosages than the comparison substances for limiting the isoprenalin tachycardia to 250 beats/min. (DE$_{250}$)

The compounds according to the present invention are thus unexpectedly superior in effectiveness to known compounds and thus present a valuable contribution to the art.

The dosages of the novel compounds of the present invention depend on the age, weight, and the condition of the patient being treated. Generally speaking, for adultoral administration, the preferred unit dosage of active compound with suitable pharmaceutical diluent or lubricant is 1 mg. to 40 mg. four times a day. In general the oral dosage is 20 to 40 mg., whereas the intravenous dosage is generally 1 to 5 mg., four times a day.

For preparing therapeutic compositions such as tablets and other compressed formulations, the compounds can include any compatible and edible tableting material used in pharmaceutical practice as for example, corn starch, lactose, stearic acid, magnesium stearate, talc, methyl cellulose and the like.

Similarly the compounds of the present invention can be mixed with suitable adjuvants for the preparation of resorbable hard gelatin or soft capsules utilizing conventional pharmaceutical practices.

Further, the compounds can be employed in the form of their solutions or suspensions suitable for parenteral administration.

It will be appreciated that the instant specification and examples are set forth by way of illustration and not limitation, and that various modifications and changes may be made without departing from the spirit and scope of the present invention.

What is claimed is:

1. Aminopropanol compound of the formula

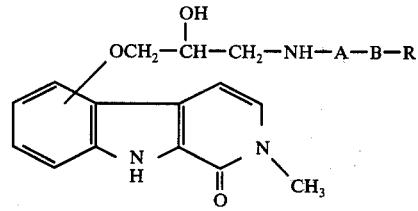

wherein
A is alkylene of from 2-6 carbon atoms,
B is sulfur or a valency bond,
R is a straight-chained or branched lower alkyl; and the pharmacologically compatible salts thereof.

2. Aminopropanol compound as claimed in claim 1 wherein A is alkylene of from 2 to 4 carbon atoms.

3. Aminopropanol compound as claimed in claim 1 wherein B is a sulfur atom.

4. Aminopropanol compound as claimed in claim 1 wherein B is a valency bond.

5. Aminopropanol compound as claimed in claim 1 wherein R is alkyl of up to 4 carbon atoms.

6. Aminopropanol compound as claimed in claim 1 designated 5-(2-hydroxy-3-isopropylaminopropoxy)-1-oxo-2-methyl-1,2-dihydro-β-carboline.

7. Aminopropanol compound as claimed in claim 1 designated 5-(2-hydroxy-3-tert.-butylaminopropoxy)-1-oxo-2-methyl-1,2-dihydro-βcarboline.

8. Aminopropanol compound as claimed in claim 1 designated 5-[2-hydroxy-3-(1-methylthio-2-methyl-isopropylamino)-propoxy]-1-oxo-2-methyl-1,2-dihydro-β-carboline.

* * * * *